United States Patent [19]
Fallin et al.

[11] Patent Number: 5,089,003
[45] Date of Patent: Feb. 18, 1992

[54] RASP TOOL INCLUDING DETACHABLE HANDLE MEMBER

[75] Inventors: Thomas W. Fallin, Cordova; Joseph H. Kang, Memphis, both of Tenn.

[73] Assignee: Zimmer, Inc., Warsaw, Ind.

[21] Appl. No.: 455,536

[22] Filed: Dec. 22, 1989

[51] Int. Cl.⁵ ............................................. A61B 17/16
[52] U.S. Cl. ....................................... 606/85; 606/53
[58] Field of Search .................. 403/328, 327, 325; 606/53, 79, 84, 85

[56] References Cited

U.S. PATENT DOCUMENTS

| | | | |
|---|---|---|---|
| D. 272,648 | 2/1984 | Bolesky et al. | D24/28 |
| D. 273,806 | 5/1984 | Bolesky et al. | D24/28 |
| D. 282,238 | 1/1986 | Kenna | D8/94 |
| D. 284,100 | 6/1986 | Kenna | D24/33 |
| 3,810,703 | 5/1974 | Pasbrig | 403/328 X |
| 3,815,599 | 6/1974 | Deyerle | 128/305 |
| 3,874,003 | 4/1975 | Moser et al. | 3/1 |
| 4,165,854 | 8/1979 | Duly | 403/328 X |
| 4,306,550 | 12/1981 | Forte | 128/92 E |
| 4,466,429 | 8/1984 | Loscher et al. | 128/92 E |
| 4,552,136 | 11/1985 | Kenna | 128/92 E |
| 4,583,270 | 4/1986 | Kenna | 29/80 |
| 4,587,964 | 5/1986 | Walker et al. | 128/92 E |
| 4,601,289 | 7/1986 | Chiarizzio et al. | 128/305 |
| 4,602,890 | 7/1986 | Duda | 403/328 X |
| 4,671,275 | 6/1987 | Deyerle | 128/305 |
| 4,739,750 | 4/1988 | Masse et al. | 128/92 VJ |
| 4,765,329 | 8/1988 | Keller et al. | 128/303 R |
| 4,917,442 | 4/1990 | Johnson | 403/328 |
| 4,921,493 | 5/1990 | Webb, Jr. et al. | 606/85 |

OTHER PUBLICATIONS

Zimmer, Inc.-Zimmer Anatomic Hip System Femoral Rasps, Sep. 1988, package insert plus related drawing.
Biomet, Inc.-Catalog pp. A-8, A-9 and related page from a brochure-Removable Rasp Handle and APF Rasp-Provisional-No date available.
Richards Medical Co.-BIO-FIT Femoral Prosthesis, Design Features and Surgical Technique-Note pp. 7 and 13 re Broach (Rasp) Trial and Broach Handle-1987.
Waldemar Link-Link Calcar Reamer DBGM-1983.
Zimmer, Inc.-BIAS Total Hip Femoral Rasps-May 1986 Package Insert, plus related drawing.
Zimmer, Inc.-The Total System Rasps (Corresponds to U.S. Pat. No. 4,587,964)-1986 (Revised 1988) Package Insert.

Primary Examiner—Robert A. Hafer
Assistant Examiner—Brian E. Hanlon
Attorney, Agent, or Firm—Margaret L. Geringer

[57] ABSTRACT

A rasp tool including a handle member, a cutter member, and a releasable locking mechanism for selectively coupling the handle and cutter members. The locking mechanism includes a locking post on the cutter member and a corresponding post-receiving bore in the handle member. A spring-biased locking key is disposed within a guide bore that intersects the post-receiving bore such that the locking key extends partially into the post-receiving bore. As the locking post is axially introduced into the post-receiving bore, the locking post contacts the locking key and causes it to retract until the locking post is fully received within the bore, at which point the spring-biased locking key engages a transverse notch in the locking post, thereby preventing axial removal of the post from the bore. The locking key is disengaged from the locking post by a manually-actuable trigger coupled to the locking key.

19 Claims, 3 Drawing Sheets

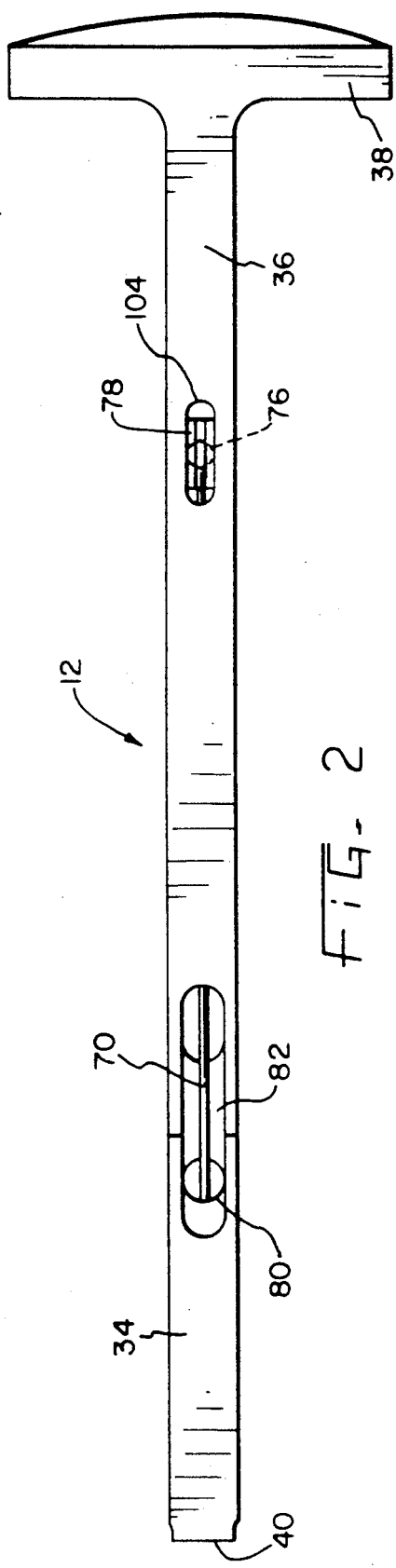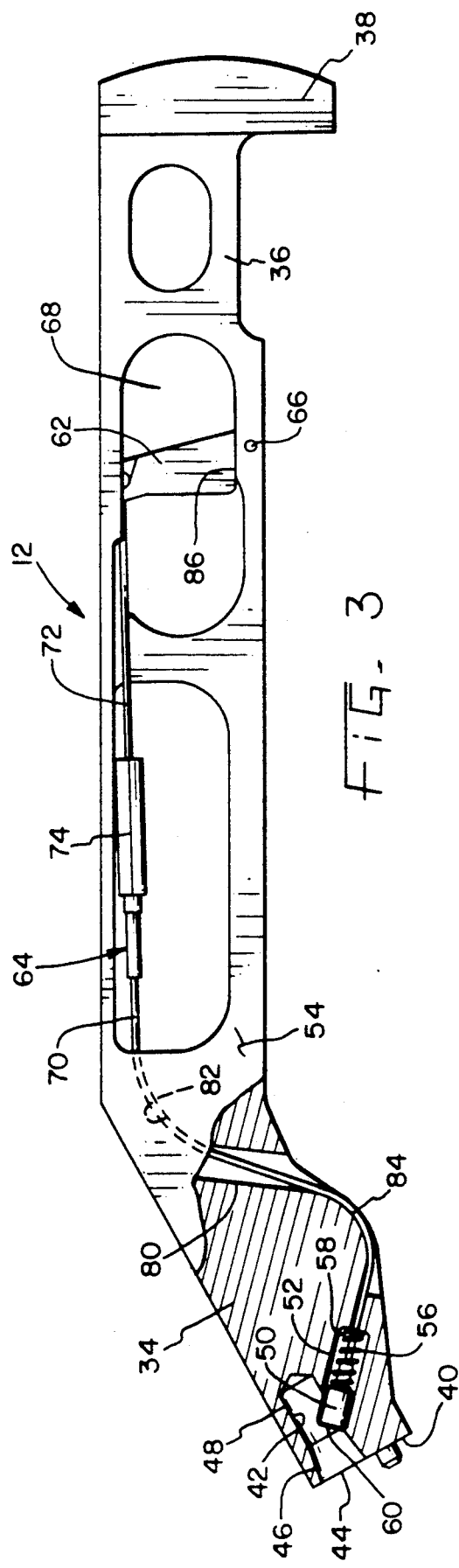

RASP TOOL INCLUDING DETACHABLE HANDLE MEMBER

BACKGROUND OF THE INVENTION

The present invention relates generally to a rasp tool of the type used by an orthopedic surgeon to contour bone or the like and, more particularly, to such a rasp tool used to prepare a femur for implantation of a femoral prosthesis.

It is known to utilize a rasp tool having a handle member that is releasable relative to a cutter member, whereby the handle can be removed after the initial rasping process of the femur. Upon removal of the handle, the cutter remains lodged in the femur to enable further contouring of the proximal end of the femur, as by calcar reaming. The cutter may then be used as a provisional or trial prosthetic implant by cooperating with mating neck/collar and head/neck provisional components in order to perform a trial joint reduction. The handle is reattached to the cutter in order to extract the cutter from the femur.

Generally, prior art rasp tools in which the cutter member is releasable relative to the handle member involve a relatively complex locking mechanism that may be difficult or cumbersome for some surgeons to operate during surgery. For example, several prior art designs require that the handle move laterally relative to the cutter in order to effect disengagement. If the cutter is countersunk in the proximal end of the femur, lateral movement of the handle may be difficult.

With respect to the manner in which the surgeon must actuate the locking mechanism, known prior art rasp tools require the same positive actuation step during both engagement and disengagement of the cutter with the handle. Depending on the particular mechanism employed, the positive actuation step may include turning and tightening, or other cumbersome steps. Furthermore, many of the prior art locking mechanisms include an actuation apparatus at the handle/cutter junction. Not only does this tend to obscure the surgeon's view of the femur during normal use of the rasp tool, but it also requires the surgeon's hand to be in the vicinity of the open wound to actuate the mechanism.

The present invention is directed to overcoming the aforementioned problems associated with prior art rasp tools. Specifically, it is desired to provide a rasp tool having a simple and reliable releasable locking mechanism that minimizes the steps required for engagement and disengagement of the cutter with the handle and provides actuation of the locking mechanism at a location that is remote from the handle/cutter junction.

SUMMARY OF THE INVENTION

The present invention overcomes the problems and disadvantages of the above-described prior art rasp tools by providing an improved releasable locking mechanism, wherein the handle and a cutter are positively locked against axial separation automatically upon initial axial engagement thereof, and are released in response to actuation of a disengaging mechanism by the surgeon.

Generally, the present invention provides a cutter having a locking post and a handle having a post-receiving bore in which the locking post is received. A locking mechanism responds to introduction of the locking post into the bore and engages the locking post to prevent axial separation of the cutter and handle. A separate disengaging mechanism is operable by the surgeon to permit axial separation of the cutter and handle.

More specifically, the present invention provides, in one form thereof, a locking post that is slidably received within a guide bore that intersects the aforementioned post-receiving bore. The locking post includes a transverse notch which the locking key engages when the locking post is fully received within the post-receiving bore. The guide bore is oriented relative to the post-receiving bore such that introduction of the locking post into the post-receiving bore causes the locking key to retract and then return to an extended position engaged with the notch of the locking post. The locking key is also retracted in response to manual actuation of a trigger by the surgeon.

An advantage of the rasp tool of the present invention is that locking interconnection between the cutter and handle is simply and easily accomplished in one step.

Another advantage of the rasp tool of the present invention, in one form thereof, is that disengagement of the handle from the cutter is accomplished at a location remote from the handle/cutter interface, thereby improving the surgeon's view of the wound and obviating the need to have the surgeon's hands in the vicinity of the wound during the disengagement step.

The rasp tool of the present invention, in one form thereof, provides a cutter member including an abutment surface and a locking post extending axially from the abutment surface. An elongate handle member is also provided, including an abutment surface at one end and a head portion at the other end. The handle member includes an axial post-receiving bore having an access opening on the abutment surface thereof. The locking post is received within the post-receiving bore in response to relative axial movement of the cutter member toward the handle member to a fully engaged position at which the abutment surfaces of the cutter and handle members are adjacent one another. A releasable locking mechanism on the handle member provides selective locking of the locking post within the post-receiving bore. Specifically, the locking mechanism includes a locking key slidably received within a guide bore formed in the handle member, wherein the guide bore intersects the post-receiving bore. The locking key is slidable within the guide bore between an extended position at which the locking key extends partially into the post-receiving bore and operatively engages the locking post, and a retracted position at which the locking key is retracted from the post-receiving bore and is disengaged from the locking post. The locking key is spring-biased toward the extended position. A disengaging mechanism on the handle means is manually actuable by the surgeon to disengage the locking key from the locking post, thereby permitting removal of the locking post from the post-receiving bore.

In one aspect of the invention, the aforementioned guide bore is angularly oriented relative to the post-receiving bore such that the locking post contacts the locking key upon initial introduction of the locking post into the post-receiving bore. As the cutter member and handle member are then moved toward their fully engaged position, the locking key is urged by the locking post from the extended position to the retracted position. The spring-biased locking key is returned to the extended position operatively engaged with the locking post upon attainment of the fully engaged position.

BRIEF DESCRIPTION OF THE DRAWINGS

FIG. 2 is an enlarged top view of the handle member of the rasp tool of FIG. 1;

FIG. 3 is an enlarged side view in partial cross-section of the handle member of the rasp tool of FIG. 1;

DESCRIPTION OF THE PREFERRED EMBODIMENT

Figure 1:
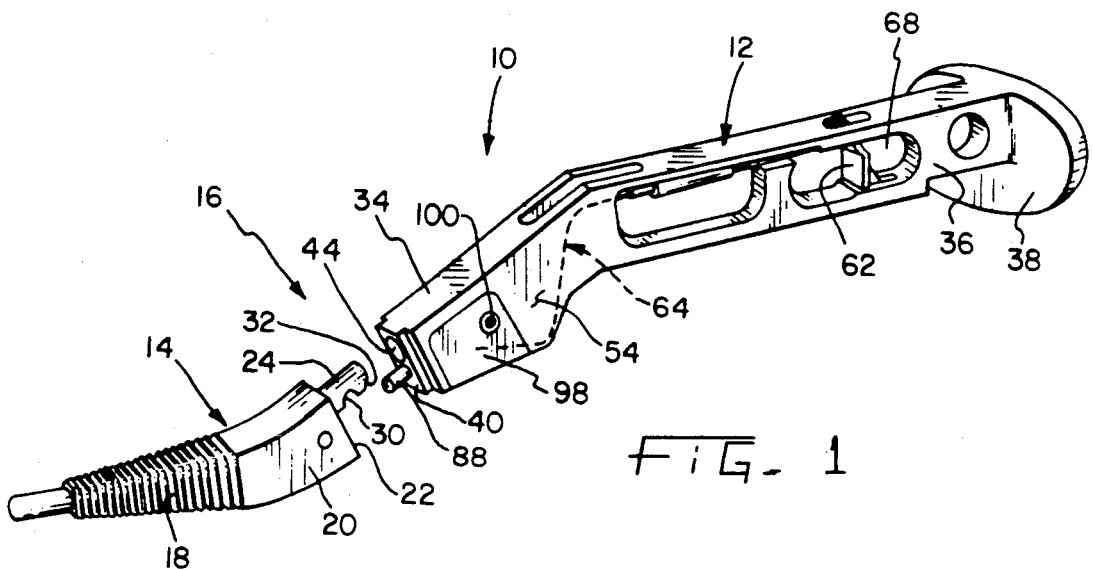
FIG. 1 is an exploded perspective view of an exemplary rasp tool that incorporates a releasable locking mechanism in accordance with the principles of the present invention.

In an exemplary embodiment of the invention as shown in the drawings, and in particular by reference to FIG. 1, a rasp tool 10 is shown including a handle 12 and a cutter 14 in the form of a femoral rasp. In accordance with the present invention, a releasable locking mechanism 16 permits selective interconnection between handle 12 and cutter 14, as will be more particularly described hereinafter.

Cutter 14 includes a rasping surface 18 and a coupling end 20, as illustrated in FIG. 1. Coupling end 20 includes a planar abutment surface 22 and a locking post 24 extending axially therefrom. Locking post 24 includes a frustoconical base portion 26 and generally cylindrical end portion 28. End portion 28 of locking post 24 includes a generally transverse V-shaped notch 30 at an intermediate location thereof, and a bevelled contact surface 32 located at the extreme end thereof.

Referring now to FIGS. 1-3, handle 12 is generally axially elongated and includes a coupling end 34 and an impact end 36 having an enlarged head 38. Coupling end 34 includes a planar abutment surface 40 and a post-receiving bore 42 having an access opening 44 on abutment surface 40. Bore 42 corresponds to and is adapted to receive locking post 24 upon axial alignment of cutter 14 and handle 12 and relative axial movement therebetween. Specifically, bore 42 includes a frustoconical base portion 46 and a generally cylindrical portion 48, which corresponds to base 26 and end 28 of locking post 24, respectively.

Locking mechanism 16 further includes a locking key 50 slidably disposed within a guide bore 52 formed in handle 12, wherein guide bore 52 intersects post-receiving bore 42, as shown in FIG. 3. In the preferred embodiment, guide bore 52 extends from its point of intersection with post-receiving bore 42 in a direction away from abutment surface 40 and at an approximate 45° angle with respect to the axis of bore 42. Guide bore 52 is preferably a rectangular slot milled into a side surface 54 of handle 12, while locking key 50 is a rectangular block indexed within guide bore 52. Locking key 50 is slidable within guide bore 52 between an extended position at which the key extends partially into post-receiving bore 42 (FIG. 3), and a retracted position at which the key does not extend into bore 42 (FIG. 4D).

Referring again to FIG. 3, one end of locking key 50 includes an actuation surface 60 adapted to initially engage bevelled contact surface 32 of locking post 24 upon introduction of the locking post into the post-receiving bore. Locking key 50 is selectively moved to its retracted position by disengaging means of the present invention, including a manually-actuable trigger 62 operatively connected to locking key 50 by a cable assembly 64. A pivot pin 66 pivotally connects one end of trigger 62 to handle 12 within a through hole 68 formed in impact end 36 of the handle. The other end of trigger 62 is connected to cable assembly 64, whereby pivotal movement of trigger 62 effects sliding movement of locking key 50 within guide bore 52.

Figure 6A:
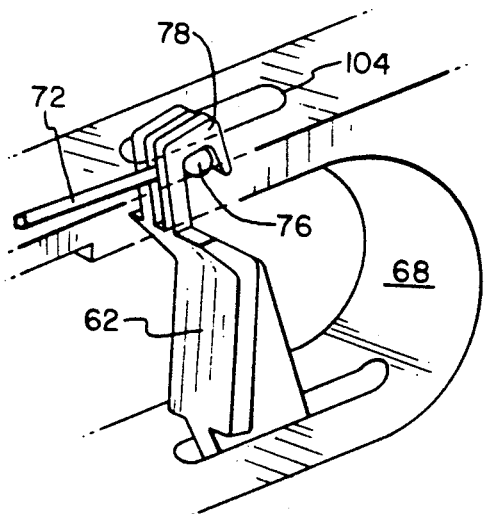
FIGS. 6A and 6B are enlarged fragmentary views of the handle member of the rasp tool of FIG. 1, particulary showing the control cable both operably coupled to the trigger and uncoupled therefrom the removal and cleaning.

Cable assembly 64 includes a pair of flexible cable portions 70 and 72 joined by a conventional turnbuckle assembly 74. More specifically, a respective one end of each of cable portions 70 and 72 is attached to a respective half of turnbuckle assembly 74. The other end of cable portion 70 is attached to locking key 50, and the other end of cable portion 72 is terminated by a swaged ball 76 coupled to a yoke portion 78 formed on the free pivoting end of trigger 62, as best shown in FIG. 6A. As illustrated in FIGS. 1-3, cable portion 72 and turnbuckle assembly 74 are openly disposed within through hole 68, while cable portion 70 extends through a cable bore 80 communicating between rounded top and bottom bearing corners 82 and 84.

A compressed coil spring 56 is disposed coaxially about cable portion 70 between locking key 50 and an end wall 58 of guide bore 52, whereby locking key 50 is urged toward post-receiving bore 42. Referring to FIG. 3, counterclockwise pivotal movement of trigger 62 about pivot pin 66 is limited by the engagement of trigger 62 with a stop surface 86. Consequently, the extended position of locking key 50 into post-receiving bore 42, i.e., when trigger 62 engages stop surface 86 and locking key 50 is urged by spring 56 into post-receiving bore 42, is determined by the length of cable assembly 64, which is adjustable by turnbuckle assembly 74.

Figure 4A:
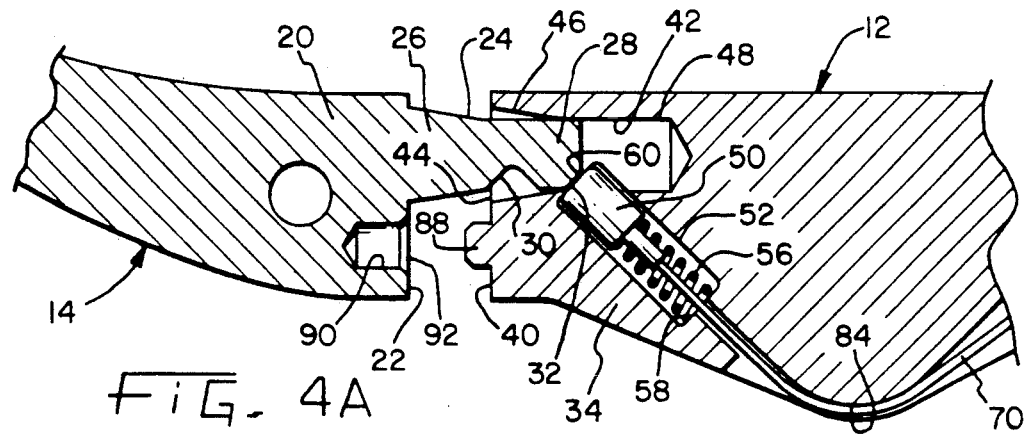
FIG. 4A-4D are enlarged fragmentary sectional views of the rasp tool of FIG. 1, particulary showing progressive stages of the interconnection between the handle and cutter members thereof.
Figure 4B:
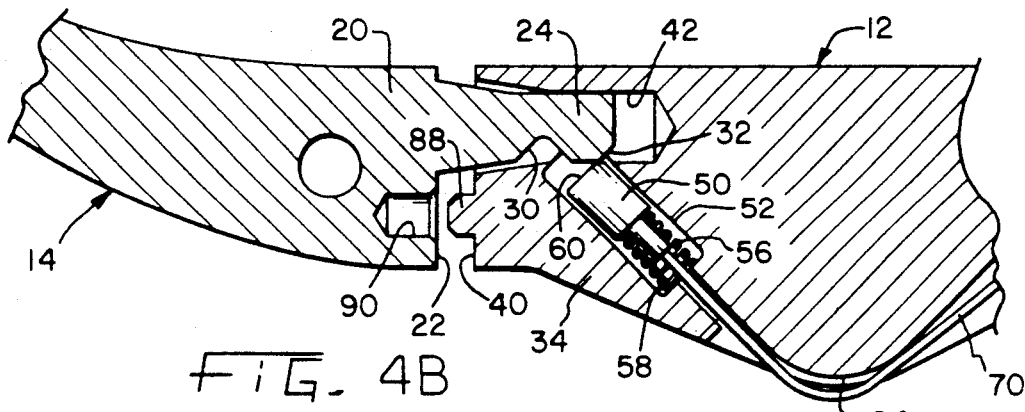
Figure 4C:
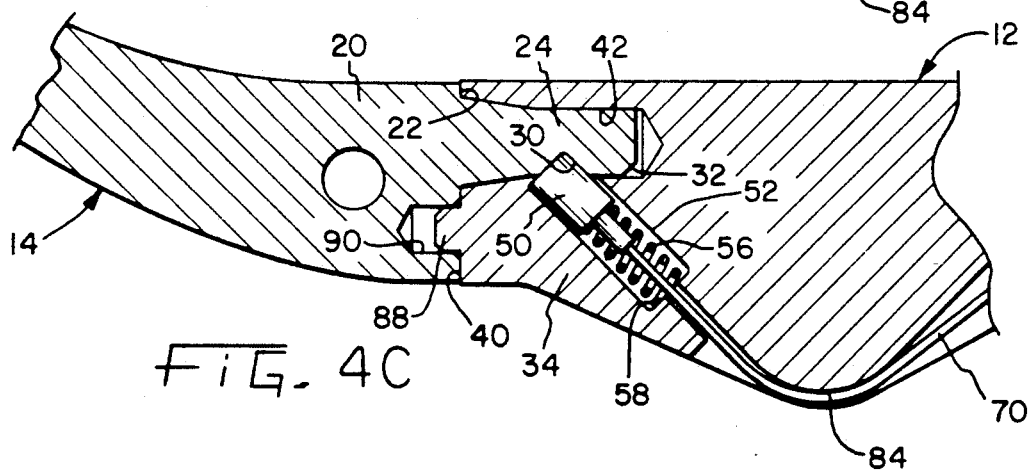
Figure 4D:
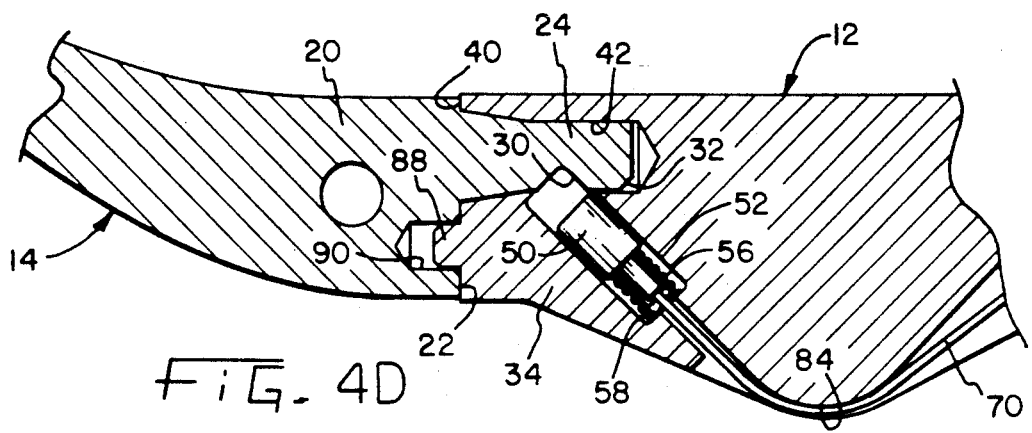

Referring now to FIGS. 4A-4D, releasable locking mechanism 16 provides automatic locking interconnection of cutter 14 and handle 12 in response to axial engagement, and manually-actuated release of locking mechanism 16 upon operation of trigger 62. In FIG. 4A, locking key 50 is shown at rest in its extended position partially within post-receiving bore 42. Locking post 24 is at the point of axial introduction into bore 42 at which contact surface 32 first engages actuation surface 60 of locking key 50 to create a sliding interface therebetween.

FIG. 4B illustrates locking key 50 at its retracted position as locking post 24 continues its axial advance into bore 42. Specifically, locking key 50 is urged by compressed spring 56 against that portion of locking post 24 intermediate contact surface 32 and notch 30. The forced retraction of locking key 50 by locking post 24, without actuation of trigger 62, tends to cause slack in cable portion 70 in the vicinity of bottom bearing corner 84, as illustrated in FIG. 4B.

FIG. 4C corresponds to complete axial engagement of cutter 14 with handle 12, at which point abutment surfaces 22 and 40 are adjacent one another. In this position, notch 30 is generally aligned with guide bore 52, whereby locking key 50 is permitted to return to its extended position under the force of spring 56. Accordingly, FIGS. 4A–4C illustrate an engagement step wherein locking key 50 is automatically retracted and then "snapped" into locking engagement with locking post 24 upon attainment of a fully engagement relationship between cutter 14 and handle 12.

The disengagement step of locking mechanism 16 is illustrated in FIG. 4D, wherein locking key 50 is now shown in its retracted position in response to manual actuation of trigger 62. During this disengagement step, cable assembly 64 is generally taut, as illustrated by the fact that cable portion 70 closely follows bottom corner bearing 84 and is not loose, as in the case of FIG. 4B. As a result of the retraction of locking key 50 from notch 30, cutter 14 is capable of being axially separated from handle 12.

In addition to the positive engagement between cutter 14 and handle 12 provided by releasable locking means 16 of the present invention, relative rotation of the members about the axis of locking post 24 and bore 42 is opposed by an alignment mechanism. Specifically, an alignment pin 88 extends axially from abutment surface 40 of handle 12, and is received within a corresponding axially aligned blind bore 90 in cutter 14 through an access opening 92 on abutment surface 22.

Referring now to FIGS. 1, 5A–5B, and 6A–6B, cable assembly 64, including locking key 50 and spring 56, is removable from handle 12 for cleaning or replacement purposes. To facilitate such removal, side surface 54 of handle 12 includes a countersunk region 94 onto which milled guide bore 52 and a cable access slot 96 open. A protective cover plate 98 fits within countersunk region 94 and is secured to handle 12 by means of a recessed cap screw 100 received within a threaded hole 102.

Figure 5A:
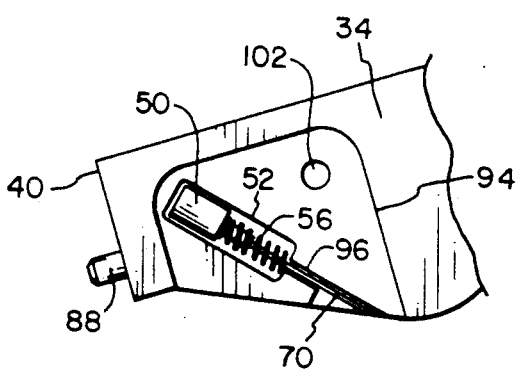
FIGS. 5A and 5B are enlarged fragmentary views of the handles member of the rasp tool of FIG. 1 with the side cover removed to expose the locking key, particularly showing the spring-biased locking key both operably assembled in the handle and removed from the handle for cleaning, respecitvely.
Figure 5B:
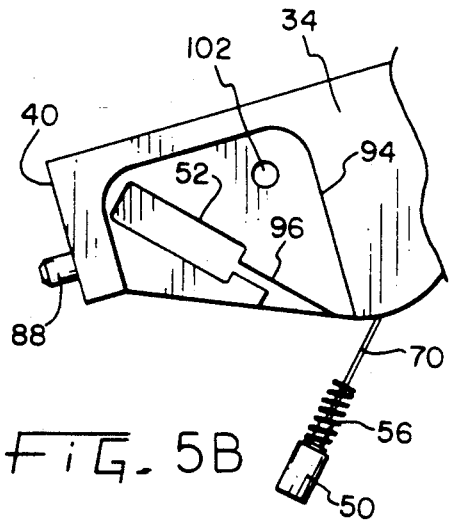
Figure 6B:
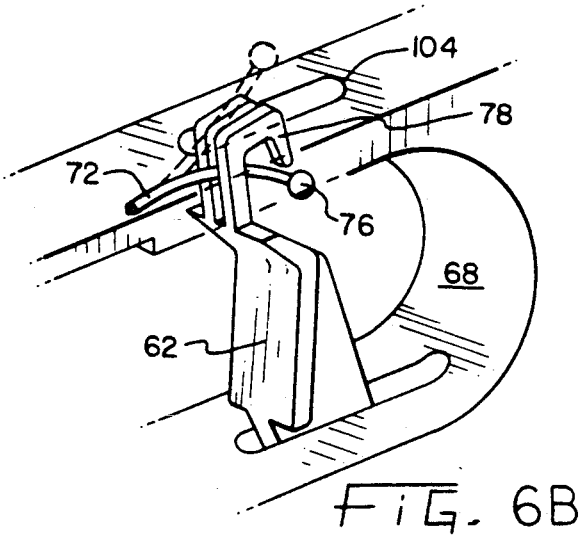

Locking key 50, together with spring 56, is removed from guide bore 52 by the passage of cable portion 70 through cable access slot 96, as illustrated in FIGS. 5A–5B. Cable assembly 64 will then become slack, thereby permitting swaged ball 76 on the end of cable portion 72 to be disengaged from trigger yoke 78, as shown in FIG. 6B. A slot 104 in handle 12, located directly adjacent trigger yoke 78, permits swaged ball 76 to pass therethrough to completely disconnect cable portion 72 from handle 12.

It will be appreciated that the foregoing description of a preferred embodiment of the invention is presented by way of illustration only and not by way of any limitation, and that various alternatives and modifications may be made to the illustrated embodiment without departing from the spirit and scope of the invention.

What is claimed is:

1. A rasp tool for use by a surgeon to contour bone or the like, comprising:

cutting means for contouring the bone, said cutting means including an axially extending locking post;

handle means, selectively connectable to said cutting means and operable by the surgeon, for imparting movement to said cutting means, said handle means comprising an elongated handle member connectable at one end thereof to said cutting means and having a head portion at the other end thereof, said handle means including a post-receiving bore adapted to axially receive said locking post therein;

releasable locking means associated with said handle means for selectively interconnecting said handle means and said cutting means against axial separation when said locking post is received within said bore, said locking means including key means for engaging said locking post within said bore in response to introduction of said locking post into said bore, said locking post includes a generally V-shaped transverse notch and said key means includes an elongate locking key having one end that extends into said notch at an acute angle relative to the axially extending locking post to operatively engage said locking post, and said elongate locking key intersecting said post receiving bore at an acute angle relative thereto; and disengaging means, associated with said handle means and manually actuable by the surgeon, said disengaging means including a manually actuable trigger located toward said other end of said handle member spaced from said cutter means for disengaging said key means from said locking post, thereby permitting removal of said locking post from said bore.

2. The rasp tool of claim 1 in which:

said cutting means includes a cutter member having an abutment surface from which said locking post extends, and said handle means includes an elongate handle member having an abutment surface at one end thereof, said post-receiving bore having an access opening on said abutment surface of said handle member, said abutment surface of said cutter member and said abutment surface of said handle member being adjacent one another when said cutting means and said handle means are operatively interconnected.

3. The rasp tool of claim 2, and further comprising:

alignment means cooperating between said cutter member and said handle member for providing operative alignment therebetween when said locking post is received within said post-receiving bore, said alignment means including an alignment pin extending from the abutment surface of one of said handle member and said cutter member into a corresponding axially aligned blind bore formed in the other of said handle member and said cutter member and having an access opening on the abutment surface thereof.

4. The rasp tool of claim 1 in which:

said locking post includes a frustoconical base portion and said post-receiving bore includes a corresponding frustoconical portion in which said frustoconical base portion of said locking post is received.

5. The rasp tool of claim 1 in which:

said locking key is movable between an extended position at which said key is operatively engaged with said locking post, and a retracted position at which said key is disengaged from said locking post, said locking key being ordinarily spring-biased toward said extended position and being movable toward said retracted position in response to introduction of said locking post into said post-receiving bore and in response to manual actuation of said disengaging means by the surgeon.

6. The rasp tool of claim 1 in which:

said trigger is connected to said locking key by means of a flexible cable assembly.

7. The rasp tool of claim 1 in which:

said handle member includes a through opening in which said trigger is disposed, whereby said trigger is intentionally actuated within said through opening and is generally protected from inadvertent actuation thereof.

8. A rasp tool for use by a surgeon to contour bone or the like, comprising:
   a cutter member including an abutment surface and a locking post extending axially from said abutment surface;
   an elongate handle member including an abutment surface at one end and a head portion at the other end, said one end including an axial post-receiving bore having an access opening on said abutment surface of said handle member, said locking post being receivable within said post-receiving bore in response to relative axial movement of said cutter member toward said handle member to a fully engaged position at which said abutment surface of said cutter member is adjacent said abutment surface of said handle member;
   releasable locking means associated with said handle member for selectively locking said locking post within said post-receiving bore to prevent axial removal of said locking post from said bore, said locking means including a locking key slidably received within a guide bore formed in said handle member and intersecting said post-receiving bore at an acute angle relative thereto, said locking key being slidable within said guide bore between an extended position at which said locking key extends partially into said post-receiving bore and operatively engages said locking post, and retracted position at which said locking key is retracted from said post-receiving bore and is disengaged from said locking post, said locking key being spring-biased toward said extending position thereof; and
   disengaging means, manually actuable by the surgeon and associated with said handle member, said disengaging means including a manually actuable trigger located toward said other end of said handle member, for disengaging said locking key from said locking post, thereby permitting removal of said locking post from said post-receiving bore.

9. The rasp tool of claim 8 in which:
   said guide bore is angularly oriented relative to said post-receiving bore such that said locking post contacts said locking key upon initial introduction of said locking post into said post-receiving bore, said locking key being urged by said locking post from said extended position toward said retracted position in response to said relative movement of said cutter member and said handle member toward said fully engaged position, and said spring-biased locking key being returned to said extended position operatively engaged with said locking post upon attainment of said fully engaged position.

10. The rasp tool of claim 9 in which:
    said locking post includes an unattached end having a contact surface thereat, and said locking key includes a distal end having an actuation surface thereat, said contact surface and said actuation surface establishing a planar sliding interface therebetween as said locking post is introduced into said post-receiving bore.

11. The rasp tool of claim 8, and further comprising:
    alignment means cooperating between said cutter member and said handle member for providing operative alignment therebetween when said locking post is received within said post-receiving bore, said alignment means including an alignment pin extending from the abutment surface of one of said handle member and said cutter member into a corresponding axially aligned blind bore formed in the other of said handle member and said cutter member and having an access opening on the abutment surface thereof.

12. The rasp tool of claim 8 in which:
    said locking post includes a frustoconical base portion and said post-receiving bore includes a corresponding frustoconical portion in which said frustoconical base portion of said locking post is received.

13. The rasp tool of claim 8 in which:
    said locking post includes a generally transverse notch, and said locking key is elongate and has one end that extends into said notch to operatively engage said locking post.

14. The rasp tool of claim 13 in which:
    said locking post is generally cylindrical, and said transverse notch is V-shaped and is formed at an axially intermediate location of said locking post.

15. The rasp tool of claim 8 in which:
    said guide bore is a substantially rectangular slot and said locking key is a substantially rectangular block.

16. The rasp tool of claim 8 in which
    said trigger being connected to said locking key by means of a flexible cable assembly.

17. The rasp tool of claim 16 in which:
    said flexible cable assembly includes a turnbuckle member intermediate two cable portions.

18. The rasp tool of claim 16 in which:
    said handle member includes a through opening in which said trigger is disposed, whereby said trigger is intentionally actuated within said through opening and is generally protected from inadvertent actuation thereof.

19. A rasp tool for use by a surgeon to contour bone or the like, comprising:
    a cutting means for contouring the bone, said cutting means including an axially extending locking post;
    handle means, selectively connectable to said cutting means and operable by the surgeon, for imparting movement to said cutting means, said handle means including a post-receiving bore having an elongate axis, and wherein the bore is adapted to axially receive said locking post therein;
    releasable locking means associated with said handle means for selectively interconnecting said handle means and said cutting means against axial separation when said locking post is received within said bore, said locking means including key means for engaging said locking post within said bore in response to introduction of said locking post into said bore, said locking post includes a generally V-shaped transverse notch and said key means includes an elongate locking key having one end that extends into said notch at an acute angle relative to the axially extending locking post to operatively engage said locking post, and said elongate locking key having an elongate axis intersecting the axis of the post receiving bore at an acute angle relative thereto; and
    disengaging means, associated with said handle means and manually actuable by the surgeon, for disengaging said key means from said locking post, thereby permitting removal of said locking post from said bore.

* * * * *